United States Patent [19]

Schrock

[11] 4,427,595
[45] Jan. 24, 1984

[54] CATALYST COMPOSITION TO EFFECT METATHESIS OF ACETYLENES

[75] Inventor: Richard R. Schrock, Brighton, Mass.

[73] Assignee: Massachusetts Institute of Technology, Cambridge, Mass.

[21] Appl. No.: 283,752

[22] Filed: Jul. 16, 1981

[51] Int. Cl.$^3$ ............................................. C07F 11/00
[52] U.S. Cl. .................................. 260/429 R; 585/534
[58] Field of Search ...................... 260/429 R; 585/534

[56] References Cited

U.S. PATENT DOCUMENTS

| | | | |
|---|---|---|---|
| 2,198,236 | 4/1940 | Vaughn | 585/534 |
| 3,432,530 | 3/1969 | Wilke | 260/429 R |
| 3,558,518 | 1/1971 | Luech | 260/429 R X |
| 3,816,491 | 6/1974 | Wilkinson | 260/429 R |
| 3,988,332 | 10/1976 | Schrock | 260/429 R |

OTHER PUBLICATIONS

Clark et al., J.A.C.S. 100 6774 (1978).

*Primary Examiner*—Helen M. S. Sneed
*Attorney, Agent, or Firm*—Arthur A. Smith, Jr.; Paul J. Cook

[57] ABSTRACT

Tungsten compounds of the formula:

$$[L_yX_{n+3}W \equiv CR^3]^{n-}(M^+)^n$$

wherein
R$^3$ is an alkyl or aryl;
L is a moiety of the formula ZR$^4$R$^5$R$^6$, (O)ZR$^4$R$^5$R$^6$, ZR$^4$R$^5$(OR$^6$), ZR$^4$(OR$^5$) (OR$^6$) or Z(OR$^4$) (OR$^5$) (OR$^6$); wherein Z is a group 5 element including N, P or As and R$^4$, R$^5$ and R$^6$ can be the same or different and are alkyl, aralkyl or aryl;
X is F, Cl, Br, I, OR$^4$, NR$^4$R$^5$ or SR$^4$;
M$^+$ is a metallic or organic cation; alkyl has 1-10 carbons, aralkyl has 7-10 carbons and aryl has 6-10 carbons;
n is 0 or 1, and y is 0, 1 or 2, with the proviso that:
y is 0 when X is OR$^4$, NR$^4$R$^5$ or SR$^4$, and n=0;
y is 0 when X is OR$^4$, F, Cl, Br or I, and n=1.

These compounds will transform unsymmetric acetylenes into a mixture containing the unsymmetric acetylene and the two possible symmetric acetylenes in their thermodynamically determined relative amounts at equilibrium. The equilibrium can involve any number of acetylenes and can be reached from any point off equilibrium.

10 Claims, No Drawings

CATALYST COMPOSITION TO EFFECT METATHESIS OF ACETYLENES

The Government has rights in this invention pursuant to Grant No. CHE 79 05307 awarded by the National Science Foundation.

BACKGROUND OF THE INVENTION

The invention relates to homogeneous catalysts for the metathesis of acetylenes (alkynes), a process which is defined as the redistribution of alkylidyne moieties in a mixture of alkynes.
For example, $$2XR'C\equiv CR^2 \rightleftharpoons R'C\equiv CR' + R^2C\equiv CR^2.$$
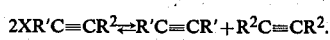

Prior to the present invention, there has been no report of a homogeneous tungsten catalyst for the metathesis of alkynes. Two types of alkyne metathesis catalysts are known, heterogeneous catalysts containing tungsten which operate inefficiently at 300°–400° C. (F. Pannella, R. L. Banks and G. C. Bailey, *J. Chem. Soc. Chem. Comm.*, 1548 (1968)), and a homogeneous catalyst system made from Mo(CO)$_6$ and phenol in toluene (A. Mortreux, J. C. Delgrange, M. Blanchard and B. Lubonchinsky, *J. Molec. Catal.* 2, 73 (1977); S. Devarajan, O. R. M. Walton and G. J. Leigh, *J. Organometal. Chem.*, 181, 99 (1979)). None of the prior art has identified the catalytically active species or site.

It would be desirable to provide a homogeneous catalyst for the metathesis of acetylenes because it, like olefin metathesis, allows manipulation of hydrocarbon feedstocks in the chemical industry.

SUMMARY OF THE INVENTION

The compounds of the present invention have the general formula:

$$[L_yX_{n+3}W\equiv CR^3]^{n-}(M^+)^n$$

wherein
R$^3$ is an alkyl or aryl;
L is a moiety of the formula ZR$^4$R$^5$R$^6$, (O)ZR$^4$R$^5$R$^6$, ZR$^4$R$^5$(OR$^6$), ZR$^4$(OR$^5$) (OR$^6$) or Z(OR$^4$) (OR$^5$) (OR$^6$), wherein Z is a group 5 element including N, P or As and R$^4$, R$^5$ and R$^6$ can be the same or different and are alkyl, aralkyl or aryl;
X is F, Cl, Br, I, OR$^4$, NR$^4$R$^5$ or SR$^4$;
M$^+$ is a metallic or organic cation; alkyl has 1–10 carbons, aralkyl has 7–10 carbons and aryl has 6–10 carbons;
n is 0 or 1 and y is 0, 1 or 2, with the proviso that:
y is 0 when X is OR$^4$, NR$^4$R$^5$ or SR$^4$, and n=0;
y is 0 when X is OR$^4$, F, Cl, Br or I, and n=1.

Examples of alkyl groups are methyl, ethyl, isopropyl, t-butyl, hexyl, octyl, decyl and neopentyl.
Examples of arylkyl groups are benzyl, p-ethylbenzyl, naphthylmethyl and diphenylmethyl.
The terms "aryl" and "ar" are employed here to denote a radical derived from a hydrocarbon, having as its only unsaturation aromatic unsaturation in six membered carbocyclic rings, by removal of a hydrogen atom from a nuclear carbon atom of an aromatic ring. Examples of aryl groups are phenyl, 1- and 2-naphthyl, o-, m-, and p-tolyl, ethylphenyl, butylphenyl, xylyl and trimethylphenyl.

Examples of M$^+$ are [NR$^3$R$^4$R$^5$R$^6$]$^+$, [PR$^3$R$^4$R$^5$R$^6$]$^+$, Li$^+$, K$^+$ or Na$^+$, preferably NEt$_4^+$, NMe$_4^+$ or PMe$_4^+$.

When X is F, Cl, Br or I, the compounds of this invention where y is 0 are prepared in accordance with reactions 1 or 2

$$(Me_3CCH_2)_3W\equiv CCMe_3 + 3HX \xrightarrow{25°\,C.} 3CMe_4 + X_3W\equiv CCMe_3 \quad (1)$$
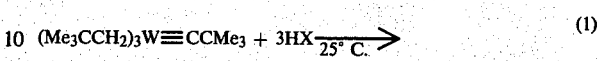
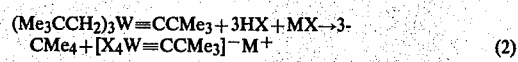

$$(Me_3CCH_2)_3W\equiv CCMe_3 + 3HX + MX \rightarrow 3CMe_4 + [X_4W\equiv CCMe_3]^-M^+ \quad (2)$$

(Me=CH$_3$); a typical solvent is diethyl ether, tetrahydrofuran, chlorobenzene or dichloromethane and a typical temperature is between about −78° C. and 50° C., preferably about 25° C. The product is recovered by filtration or by removing the solvent in vacuo. Two compounds of this invention which are prepared in accordance with reactions 1 and 2 are shown in equations 3 and 4 (Et=C$_2$H$_5$).

$$(Me_3CCH_2)_3W\equiv CCMe_3 + 3HCl \rightarrow 3CMe_4 + Cl_3W\equiv CCMe_3 \quad (3)$$
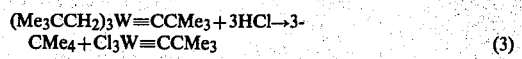

$$(Me_3CCH_2)_3W\equiv CCMe_3 + 3HCl + NEt_4^+Cl^- \rightarrow 3CMe_4 + [Cl_4W\equiv CCMe_3]^-NEt_4^+ \quad (4)$$
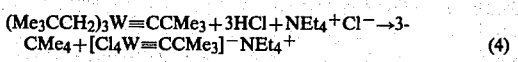

Reactions 3 and 4 can be conducted in ether solvent at a temperature between about −78° C. and 25° C. The product is recovered by filtration.

Compounds in which X is Cl or Br and which contain L are prepared in accordance with reaction 5. Two compounds of this
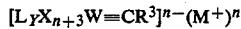

$$[X_{n+3}W\equiv CCMe_3]^{n-} + yL \rightarrow nx^- + L_yX_3W\equiv CCMe_3 \quad (5)$$
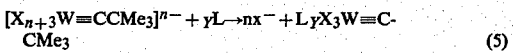

invention which are prepared in accordance with reaction 5 are shown in equations 6 and 7.

$$[Cl_4W\equiv CCMe_3]^- + 3PMe_3 \rightarrow Cl^- + Cl_3(PMe_3)_3W\equiv CCMe_3 \quad (6)$$
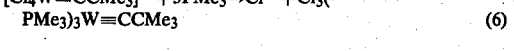

$$[Cl_4W\equiv CCMe_3]^- + (O)PMe_3 \rightarrow Cl^- + Cl_3[(O)PMe_3]W\equiv CCMe_3 \quad (7)$$
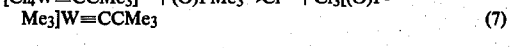

These reactions can be conducted in a tetrahydrofuran or toluene solvent at a temperature between about −78° C. and 25° C. The product is recovered by filtration.

Compounds in which X is OR$^4$, NR$^4$R$^5$ or SR$^4$ are prepared as shown in equation 8. Preparation of a typical compound of this $$[Cl_4W\equiv CCMe_3]^- + 3MX \rightarrow Cl^- + 3MCl + X_3W\equiv CCMe_3 \quad (8)$$
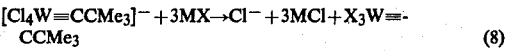

invention is shown in equation 9.

$$[Cl_4W\equiv CCMe_3]^- + 3LiOCMe_3 \rightarrow Cl^- + 3LiCl + (Me_3CO)_3W\equiv CCMe_3 \quad (9)$$
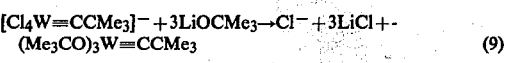

Reaction 9 can be conducted in tetrahydrofuran solvent at a temperature between about −78° C. and 25° C. The product is recovered by sublimation.

Compounds of this invention in which R$^3$ is t-butyl can be prepared by the reaction shown in equation 10 where 1 is 4

$$[L_yX_{n+3}W\equiv CR^3]^{n-}(M^+)^n + R^4C\equiv CR^5 \rightarrow R^1C\equiv CCMe_3 + [L_yX_{n+3}W\equiv CR^m]^{n-}(M^+)^n \quad (10)$$

if m is 5, and vice versa, or $R^4$ and $R^5$ are identical. Typical compounds of this invention which can be prepared in accordance with reaction 10 can be prepared as shown in reactions 11 and 12

$$Cl_3(PMe_3)_3W\equiv CCMe_3 + PhC\equiv CPh \rightarrow PhC\equiv CCMe_3 + Cl_3(PMe_3)_3W\equiv CPh \quad (11)$$

$$(Me_3CO)_3W\equiv CCMe_3 + EtC\equiv CEt \rightarrow EtC\equiv CCME_3 + (Me_3CO)_3W\equiv CEt \quad (12)$$

(Ph is phenyl).

The reactions shown in equations 10, 11 and 12 constitutute alkyne metathesis when one or more alkynes are present in excess as shown in equations 13 and 14 (all ligands except $\equiv CR$ $$W\equiv CR^5 + R^4C\equiv CR^5 \rightarrow W\equiv CR^4 + R^5C\equiv CR^5 \quad (13)$$

$$W\equiv CR^4 + R^4C\equiv CR^5 \rightarrow W\equiv CR^5 + R^4C\equiv CR^4 \quad (14)$$

omitted). The sum of equations 13 and 14 is the catalyzed reaction shown in equation 15. The reaction can run in reverse and $$2R^4C\equiv CR^5 \rightarrow R^4C\equiv CR^4 + R^5C\equiv CR^5 \quad (15)$$

the position of equilibrium which is attained in a closed system depends on the Gibbs free energy of formation of the constituent alkynes. This equilibrium can be displaced by the usual techniques such as removing one of the component alkynes. The alkyne metathesis reaction can be run in neat alkyne or in solvents such as pentane, diethyl ether or toluene, at a temperature from $-78°$ C. to $150°$ C. The product is recovered by fractional distillation.

The reactions set forth above are conducted in the absence of oxygen and moisture in order to maximize production of product. Typically, the reactions can be conducted in an atmosphere of dry nitrogen or dry inert gas.

The catalysts of this invention are particularly useful for producing acetylenes containing 18 to 20 carbon atoms in the chain which, in turn, are useful as starting materials for making detergents.

SPECIFIC EMBODIMENTS OF THE INVENTION

This invention is further illustrated by the following examples, which should not, however, be construed as fully delineating the scope of this discovery.

In order to avoid the presence of oxygen and moisture, all experiments below were carried out in an atmosphere of dry molecular nitrogen.

Trineopentylneopentylidyne tungsten, $(Me_3CCH_2)_3W\equiv CCMe_3$, was prepared by reacting six equivalents of neopentyllithium with $WCl_6$ in ether (Clark and Schrock, *J. Am. Chem. Soc.*, 100, 6774 (1978)).

In the examples below $Me=CH_3$, $Ph=C_6H_5$, $Et=C_2H_5$, and $tol=para-C_6H_4Me$.

EXAMPLE I

Preparation of $[Et_4N]^+[W(CCMe_3)Cl_4]^-$

An ether solution of HCl (12 ml, 1 M) was added dropwise at $-20°$ to a stirred dichloromethane solution of $W(CCMe_3)(CH_2CMe_3)_3$ (1.88 g, 4 mmol) and $Et_4N^+Cl^-$ (0.66 g, 4 mmol). The reaction was warmed to room temperature and the blue precipitate filtered off and recrystallized from dichloromethane at $-30°$; yield 1.73 g (82%) $[Et_4N]^+[W(CCMe_3)Cl_4]^-$.

Anal. Calcd for $WC_{13}H_{29}Cl_4N$: C, 29.74; H, 5.57. Found: c, 30.28; H, 5.69. $^{13}C$ NMR (ppm, $CD_2Cl_2$): 337 (s, $CCMe_3$), 52.4 (t, $NCH_2CH_3$), 45.7 (s, $CCMe_3$), 33.5 (q, $CCMe_3$), 7.2 (q, $NCH_2CH_3$).

EXAMPLE II

Preparation of $W(CCMe_3)Cl_3(OPEt_3)$

A solution of $W(CCMe_3)(CH_2CMe_3)_3$ (0.50 g, 0.537 mmol) and $OPEt_3$ (0.14 g, 1.07 mmol) in 10 ml toluene was cooled to $-78°$ C. 2.1 M HCl in ethyl ether (1.67 ml, 3.50 mmol) was added slowly by syringe to this yellow-orange solution. A blue-green color was generated and after 5 minutes, a blue solid precipitated from solution. This solid was collected by filtration and washed with ether; total yield 0.43 g (81%) of $W(CCMe_3)Cl_3(OPEt_3)$.

$^1H$ NMR (ppm, $CDCl_3$, 250 MHz): 2.16 (m, 6, $PCH_2CH_3$), 1.31 (m, 9, $PCH_2CH_3$), 1.22 (s, 9, $CMe_3$). $^{13}C$ NMR (ppm, $CDCl_3$, gated $^1H$ decoupled, 62.8 MHz): 329.3 (s, $J_{CW}=209$ Hz, $CCMe_3$), 46.1 (s, $CCMe_3$), 34.9 (q, $J_{CH}=127$ Hz, $CCMe_3$), 17.9 (dt, $J_{CP}=66.6$ Hz, $J_{CH}=124$ Hz, $OPCH_2CH_3$), 5.6 (q, $J_{CH}=124$ Hz, $OPCH_2CH_3$). $^{31}P\{^1H\}$ NMR (ppm, $CDCl_3$, 36.2 MHz): 82.4 (s).

EXAMPLE III

Preparation of $W(CCMe_3)Cl_3(PMe_3)_3$ $PMe_3$ (1.0 ml, 10.5 mmol) was added by syringe to a solution of $W(CCMe_3)Cl_3(OPEt_3)$ (1.71 g, 3.46 mmol) in 5 ml tetrahydrofuran. The color of the solution turned from blue to yellow, and after 5 minutes, yellow crystals formed in the solution. This product was collected by filtration and recrystallized from a mixture of dichloromethane and pentane at $-30°$ C.; total yield 1.89 g (93%) $W(CCMe_3)Cl_3(PMe_3)_3$. $W(CCMe_3)Cl_3(PMe_3)_3$ also can be prepared by adding excess $PMe_3$ to $[NEt_4]^+[W(CCMe_3)Cl_4]^-$.

Anal. Calcd for $WC_{14}H_{36}Cl_3P_3$: C, 28.62; H, 6.18. Found: C, 29.08; H, 6.25. $^1H$ NMR (ppm, $CDCl_3$, $-20°$ C., 250 MHz): 1.66 (t, 3, $J_{HP}=9.8$ Hz, $PMe_3$), 1.42 (s, 1, $CMe_3$). $^{13}C$ NMR (ppm, $CDCl_3$, $-20°$ C., gated $^1H$ decoupled, 62.8 MHz): 400.5 (q, $J_{CP}=39.7$ Hz, $CCMe_3$), 56.7 (s, $CCMe_3$), 34.4 (q, $J_{CH}=125$ Hz, $CCMe_3$), 18.7 (qq, $J_{CP}=11.6$ Hz, $J_{CH}=137$ Hz, $PMe_3$). $^{31}P\{^1H\}$ NMR (ppm, $CDCl_3$, $-80°$ C., 36.2 MHz): 19.4 (s, $J_{PW}=247$ Hz).

EXAMPLE IV

Preparation of $W(CCMe_3)Cl_3(PEt_3)(OPEt_3)$ $PEt_3$ (0.25 g, 2.12 mmol) was added to a solution of $W(CCMe_3)Cl_3(OPEt_3)$ (0.85 g, 1.73 mmol) in 5 ml tetrahydrofuran. The color of the solution changed from blue to green-blue. The reaction mixture was filtered, and the solvent was removed in vacuo to yield oily blue-green crystals. This product was recrystallized from a mixture of ether and pentane to yield 0.95 g (90%) of blue, crystalline $W(CCMe_3)Cl_3(PEt_3)(OPEt_3)$.

Anal. Calcd for $WC_{17}H_{39}Cl_3OP_2$: C, 33.38; H, 6.43. Found: C, 33.70; H, 6.46. $^1H$ NMR (ppm, $C_6D_6$, 250 MHz): 1.82 (dq, 2, $J_{HH}=7.7$ Hz, $J_{HP}=8.3$ Hz, OPCH$_2$CH$_3$), 1.61 (dq, 2, J$_{HH}$=7.7 Hz, J$_{HP}$=6.3 Hz, PCH$_2$CH$_3$), 1.37 (s, 3, CMe$_3$), 1.00 (tq, 3, J$_{HH}$=7.4 Hz, J$_{HP}$=14.7 Hz, OPCH$_2$CH$_3$), 0.88 (tq, 3, J$_{HH}$=7.4 Hz, J$_{HP}$=16.9 Hz, OPCH$_2$CH$_3$). $^{13}$C NMR (ppm, C$_6$D$_6$, gated $^1$H decoupled, 62.8 MHz): 339.5 (d, J$_{CP}$=14.5 Hz, CCMe$_3$), 46.9 (s, CCMe$_3$), 35.1 (q, J$_{CH}$=128 Hz, CCMe$_3$), 19.1 (dt, J$_{CP}$=58.1 Hz, J$_{CH}$=128 Hz, OPCH$_2$CH$_3$), 18.5 (dt, J$_{CP}$=23.3 Hz, J$_{CH}$=131 Hz, OPCH$_2$CH$_3$), 7.2 (q, J$_{CH}$=125 Hz, PCH$_2$CH$_3$), 5.9 (q, J$_{CH}$=128 Hz, OPCH$_2$CH$_3$). $^{31}$P {$^1$H} NMR (ppm, C$_6$D$_6$, 36.2 MHz): 63.9 (s, OPEt$_3$), 33.2 (s, J$_{PW}$=256 Hz, PEt$_3$). IR: $\nu_{O=P}$=1117 cm$^{-1}$.

EXAMPLE V

Preparation of W(CCMe$_3$)(OCMe$_3$)$_3$

[Et$_4$N]$^+$[W(CCMe$_3$)Cl$_4$]$^-$ (2.0 g, 3.8 mmol) was added in small portions as a solid to 40 ml of tetrahydrofuran containing 1.28 g (11.4 mmol) KOCMe$_3$. After addition was complete the reaction mixture was stirred for one hour and filtered through Celite. The solvent was removed in vacuo and the yellow residue was sublimed at 60° (5 μ) to give 1.35 g (75%) W(CCMe$_3$)(OCMe$_3$)$_3$.

$^{13}$C NMR (ppm, CDCl$_3$): 271.3 (s, CCMe$_3$), 78.6 (s, OCMe$_3$), 49.5 (s, CCMe$_3$), 33.9 (q, CCMe$_3$), 32.3 (q, OCMe$_3$).

EXAMPLE VI

Preparation of [Et$_4$N]$^+$[W(CCMe$_3$)(OPh)$_4$]$^-$

[Et$_4$N]$^+$[W(CCMe$_3$)Cl$_4$]$^-$ (0.52 g, 1 mmol) was added to a solution of tetrahydrofuran containing 0.4 g (4 mmol) LiOPh. The reaction mixture was filtered through Celite and the solvents were removed from the filtrate in vacuo to give a yellow oil which was converted into a microcrystalline yellow powder on addition of ethyl ether; yield ~80% [Et$_4$N]$^+$[W(CCMe$_3$)(OPh)$_4$]$^-$.

$^{13}$C NMR (ppm, CH$_3$CN): 290.3 (s, CCMe$_3$), 169.2, 128.2, 121.0, 118.5 (phenyl carbon resonances), 52.3 (t, NCH$_2$CH$_3$), 47.7 (s, CCMe$_3$), 34.1 (q, CCMe$_3$).

EXAMPLE VII

Preparation of W(CPh)Cl$_3$(PMe$_3$)$_3$

A solution containing W(CCMe$_3$)(Cl$_3$)(OPEt$_3$) (0.43 g, 0.866 mmol) and diphenylacetylene (0.18 g, 1.0 mmol) in 2 ml of tetrahydrofuran was heated to 60° C. for 2 hours. During this time, the color of the reaction mixture changed from blue to green. Phenyl-t-butylacetylene (100% yield versus tungsten) was observed in the reaction mixture by gas chromatography. The reaction mixture was filtered and PMe$_3$ (0.30 ml, 3.0 mmol) was added by syringe. The color of the solution turned yellow, and after the addition of 2 ml pentane, yellow crystals precipitated from solution. The product was collected by filtration and was recrystallized from a mixture of tetrahydrofuran and pentane at −30° C.; total yield 0.47 g (89%) W(CPh)Cl$_3$(PMe$_3$)$_3$.

$^1$H NMR (ppm, CDCl$_3$, 250 MHz): 7.38 and 7.09 (m, 5, phenyl proton resonances), 1.56 (s, 27, PMe$_3$). $^{13}$C NMR (ppm, CDCl$_3$, gated $^1$H decoupled, 62.8 MHz): 356.8 (q, J$_{CP}$=43.6 Hz, CPh), 148.0, 128.1, and 126.5 (phenyl carbon resonances), 16.5 (qq, J$_{CP}$=11.6 Hz, J$_{CH}$=128 Hz, PMe$_3$). $^{31}$P{$^1$H} NMR (ppm, CDCl$_3$, 36.2 MHz): 16.7 (s, J$_{PW}$=224 Hz).

EXAMPLE VIII

Preparation of W(CPh)Cl$_3$(PEt$_3$)(OPEt$_3$)

A solution of W(CCMe$_3$)Cl$_3$(OPEt$_3$) (0.43 g, 0.866 mmol) and diphenylacetylene (0.18 g, 1.0 mmol) in 2 ml of tetrahydrofuran was heated to 60° C. for 2 h. The color of the reaction mixture changed from blue to green. Phenyl-t-butylacetylene (100%) was observed in the reaction by gas chromatography. The reaction mixture was filtered and PEt$_3$ (0.12 g, 1.0 mmol) was added. The reaction mixture was again filtered, and all volatiles removed in vacuo to yield a green oil. This oil was dissolved in a minimal amount of ether, and an equal volume of pentane was added. Blue-green crystals precipitated from this solution at −30° C.; total yield 0.44 g (80%) W(CPh)Cl$_3$(PEt$_3$)(OPEt$_3$).

$^1$H NMR (ppm, C$_6$D$_6$, 250 MHz): 7.47, 6.90, and 6.67 (m, 5, J$_{HH}$=7.4 Hz, phenyl proton resonances), 2.00 (m, 12, PCH$_2$CH$_3$ and OPCH$_2$CH$_3$), 1.21 (dt, 9, J$_{HH}$=6.6 Hz, J$_{HP}$=17.7 Hz, OPCH$_2$CH$_3$), 1.11 (dt, 9, J$_{HH}$=7.4 Hz, J$_{HP}$=15.1 Hz, PCH$_2$CH$_3$). $^{13}$C NMR (ppm, C$_6$D$_6$, gated $^1$H decoupled, 62.8 MHz): 321.9 (bs, CPh), 138.6, 137.8, 129.7, and 124.8 (m, phenyl carbon resonances), 17.9 (dt, J$_{CP}$=66.9 Hz, J$_{CH}$=125 Hz, OPCH$_2$CH$_3$), 17.1 (dt, J$_{CP}$=26.2 Hz, J$_{CH}$=125 Hz, PCH$_2$CH$_3$), 6.9 (q, J$_{CH}$=128 Hz, PCH$_2$CH$_3$), 4.8 (q, J$_{CH}$=128 Hz, OPCH$_2$CH$_3$). $^{31}$P{$^1$H} NMR (ppm, C$_6$D$_6$, 36.2 MHz): 66.3 (s, OPEt$_3$), 39.1 (s, J$_{PW}$=256 Hz, PEt$_3$). IR: $\nu_{O=P}$=1124 cm$^{-1}$.

EXAMPLE IX

Preparation of W(CPh)(OCMe$_3$)$_3$

Diphenylacetylene (0.36 g, 2 mmol) was added to a pentane solution (5 ml) of W(CCMe$_3$)(OCMe$_3$)$_3$. After three hours the volatiles were removed from the reaction in vacuo and the residue was sublimed at 80° C. (2μ); yield 80% of yellow W(CPh)(OCMe$_3$)$_3$.

$^{13}$C NMR (ppm, CDCl$_3$): 257.2 (s, CPh), 147.6, 128, 127, 125 (phenyl carbon resonances), 80.8 (s, OCMe$_3$), 32.4 (q, OCMe$_3$).

EXAMPLE X

Metathesis of 3-heptyne by W(CCMe$_3$)(OCMe$_3$)$_3$

W(CCMe$_3$)(OCMe$_3$)$_3$ (50 mg) was added to 13.0 g of 3-heptyne at 25°. After one minute the reaction mixture was passed down a column of activated alumina to remove the catalyst. The colorless effluent consisted of 13.0 g of a 1:2:1 mixture of 3-hexyne, 3-heptyne, and 4-octyne, respectively, by quantitative gas chromatographic analysis and comparison with authentic samples. It contained the expected amount of equal parts Me$_3$CC≡CEt and Me$_3$CC≡CPr by gas chromatography. A mixture of W(CPr)(OCMe$_3$)$_3$ and W(CEt)(OCMe$_3$)$_3$ could be observed by $^{13}$C NMR after removing all volatiles in vacuo from a reaction mixture.

EXAMPLE XI

Metathesis of phenyltolylacetylene by W(CCMe$_3$)(OCMe$_3$)$_3$

Phenyltolylacetylene (2.50 g) was dissolved in toluene and 41 mg of W(CCMe$_3$)(OCMe$_3$)$_3$ (0.075 mmol) was added. After one hour the solution contained 0.037 mmol of Me$_3$CC≡CPh, 0.037 mmol of Me$_3$CC≡Ctol, and 2.50 g of a 1:2:1 mixture of diphenylacetylene, phenyltolylacetylene, and ditolylacetylene, respectively. A mixture of W(CPh)(OCMe₃)₃ and W(Ctol)(OCMe₃)₃ could be observed in the reaction mixture by ¹³C NMR.

EXAMPLE XII

Metathesis of phenyltolylacetylene by W(CCMe₃)Cl₃(OPEt₃)

Phenyltolylacetylene (3.5 g) was added to a solution of W(CCMe₃)Cl₃(OPEt₃) (0.17 mmol) in 2 ml of tetrahydrofuran. After heating the reaction at 60° for two hours a 1:2:1 mixture of diphenylacetylene, phenyltolylacetylene, and ditolylacetylene was generated.

I claim:

1. A compound of the formula

wherein $R^3$ is an alkyl or aryl;

L is a moiety of the formula $ZR^4R^5R^6$ wherein Z is selected from the group consisting of nitrogen and phosphorous and $R^4$, $R^5$ and $R^6$ can be the same or different and are alkyl, aralkyl or aryl;

L is a moiety of the formula $OZR^4R^5R^6$, $ZR^4R^5R^6$, $ZR^4R^5(OR^6)$, $ZR^4(OR^5)(OR^6)$ or $Z(OR^4)(OR^5)(OR^6)$;

X is F, Cl, Br, I, $OR^4$, $NR^4R^5$ or $SR^4$;

$M^+$ is selected from the group consisting of $[NR^3R^4R^5R^6]^+$, $[PR^3R^4R^5R^6]^+$, $li^+$, $K^+$ or $Na^+$;

alkyl has 1–10 carbons, aralkyl has 7–10 carbons and aryl has 6–10 carbons;

n is 0 or 1;

y is 0, 1 or 2;

with the proviso that y is 0 when X is $OR^4$, $NR^4R^5$ or $SR^4$, and n=0;

y is 0 when X is $OR^4$, F, Cl, Br or 1, and n=1.

2. The compound of the formula $[Et_4N]^+[W(CCMe_3)Cl_4]^-$.

3. The compound of the formula W(CCMe₃)Cl₃(OPEt₃).

4. The compound of the formula W(CCMe₃)Cl₃(PMe₃)₃.

5. The compound of the formula W(CCMe₃)Cl₃(PEt₃)(OPEt₃).

6. The compound of the formula W(CCMe₃)(OCMe₃)₃.

7. The compound of the formula $[Et_4N]^+[W(CCMe_3)(OPh)_4]^-$.

8. The compound of the formula W(CPh)Cl₃(PMe₃)₃.

9. The compound of the formula W(CPh)Cl₃(PEt₃)(OPEt₃).

10. The compound of the formula W(CPh)(OCMe₃)₃.

* * * * *